US010703805B2

(12) United States Patent
Rincon et al.

(10) Patent No.: US 10,703,805 B2
(45) Date of Patent: Jul. 7, 2020

(54) MOLECULAR IMPRINTING OF WEST NILE ANTIBODIES WITH PHYSIOLOGICAL PH MATCHING

(71) Applicant: Board of Regents, The University of Texas System, Austin, TX (US)

(72) Inventors: Julio Rincon, Sunland Park, NM (US); Thomas Boland, El Paso, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 405 days.

(21) Appl. No.: 15/366,517

(22) Filed: Dec. 1, 2016

(65) Prior Publication Data

US 2017/0081394 A1 Mar. 23, 2017

Related U.S. Application Data

(63) Continuation-in-part of application No. 14/452,765, filed on Aug. 6, 2014.

(Continued)

(51) Int. Cl.

*C07K 16/10* (2006.01)
*B01J 20/10* (2006.01)

(Continued)

(52) U.S. Cl.

CPC ......... *C07K 16/1081* (2013.01); *B01J 20/103* (2013.01); *B01J 20/3057* (2013.01);

(Continued)

(58) Field of Classification Search

CPC ......................... B01J 20/3057; C07K 16/1081
See application file for complete search history.

(56) References Cited

U.S. PATENT DOCUMENTS

| | | | |
|---|---|---|---|
| 6,251,280 | B1 | 6/2001 | Dai et al. |
| 6,310,110 | B1 | 10/2001 | Markowitz et al. |

(Continued)

FOREIGN PATENT DOCUMENTS

| | | | |
|---|---|---|---|
| WO | 0155095 | A1 | 8/2001 |

OTHER PUBLICATIONS

Mathew et al., "Molecular Imprinting Approach for the Recognition of Adenine in Aqueous medium and Hydrolysis of Adenosine 5'Triphosphate," Bioconjugate Chem., 1995, 6, 524-528. (Year: 1995).*

*Primary Examiner* — Catherine S Branch
(74) *Attorney, Agent, or Firm* — Norton Rose Fulbright US LLP

(57) ABSTRACT

Methods and devices for molecular imprinting include a molecular imprinting synthesis and matching a physiological pH of a template utilized in the molecular imprinting synthesis to achieve molecular imprinting. Molecular imprinting can be achieved by matching the physiological pH of the template used in a molecular imprinting synthesis. Furthermore, electrostatic charges can be complementary matched to the template, by obtaining crystallographic data of a protein template. Particularly, positively and negatively charged amino acids can be counted and matched by an oppositely charged monomer. For hydrophobic amino acids, isoleucin, leucin, and valine amino acids are counted. Since not all hydrophobic amino acids are exposed, the hydrophobic amino acid and hydrophobic monomer ratio can be determined experimentally by varying ratios from 1:1 to 1:10.

8 Claims, 3 Drawing Sheets

Related U.S. Application Data

(60) Provisional application No. 61/892,719, filed on Oct. 18, 2013.

(51) Int. Cl.
*B01J 20/30* (2006.01)
*A61K 39/00* (2006.01)

(52) U.S. Cl.
CPC .......... *A61K 39/00* (2013.01); *G01N 2333/18* (2013.01); *G01N 2600/00* (2013.01)

(56) References Cited

U.S. PATENT DOCUMENTS

| | | |
|---|---|---|
| 6,380,266 B1 | 4/2002 | Katz et al. |
| 6,583,191 B2 | 6/2003 | Markowitz et al. |
| 6,660,780 B2 | 12/2003 | Markowitz et al. |
| 6,713,416 B2 | 3/2004 | Markowitz et al. |
| 6,881,804 B1 | 4/2005 | Sellergren et al. |
| 7,122,122 B2 | 10/2006 | Marquez-Sanchez et al. |
| 7,598,087 B2 | 10/2009 | Bright |
| 8,377,717 B2 | 2/2013 | Bright |
| 2002/0065334 A1 | 5/2002 | Markowitz et al. |
| 2001/0157209 | 8/2004 | Yilmaz et al. |
| 2012/0136180 A1 | 5/2012 | Roth et al. |
| 2012/0270964 A1 | 10/2012 | Piletsky et al. |

\* cited by examiner

MOLECULAR IMPRINTING OF WEST NILE ANTIBODIES WITH PHYSIOLOGICAL PH MATCHING

CROSS-REFERENCE TO PATENT APPLICATION

This patent application is a continuation-in-part of U.S. patent application Ser. No. 14/452,765 entitled "Molecular Imprinted Colored Silica Beads," which was filed on Aug. 6, 2014, the disclosure of which is incorporated herein by reference in its entirety. of U.S. patent application Ser. No. 14/452,765 claims priority to U.S. Provisional Patent Application Ser. No. 61/892,719 filed on Oct. 18, 2013, the disclosure of which is also incorporated herein by reference in its entirety. This patent application therefore claims priority to and the benefit of U.S. Provisional Patent Application Ser. No. 61/892,719 filed on Oct. 18, 2013.

STATEMENT OF GOVERNMENT RIGHTS

This invention was made with United States Government support under NIH (National Institutes of Health) Contract Number 5G12MD007592-20. The United States Government has certain rights in this invention.

TECHNICAL FIELD

Embodiments are related to the field of molecular imprinting. Embodiments further relate to the production of bio-inspired artificial antibodies with molecular imprinted silica particles.

BACKGROUND

Since the advent of molecular imprinting 20 years ago, there are still challenges when imprinting larger than 1,500 Da molecules. The imprinting process is hindered by multiple factors such as: size, molecule complexity, and conformational structure of the template. In addition, the majority of imprinting technologies involve organic solvents. Because of the aggressive synthesis environment, a protein template might denature before an imprint is formed. If the synthesis of molecular imprinted polymers (MIPs) were to occur at an environment where the template were to subsist for as long as the formation of the imprint, however, potentially larger imprints from active biomolecules and antibodies may be fabricated.

Imprinting of larger molecules has long been recognized for its potential to be used in diagnostic devices especially in low resource settings commonly found in many developing countries. Currently, lateral flow assays are used in low-resource settings because of their speed, ease of use, and relative low cost. Unfortunately, these assays have multiple limitations, such as poor sensitivity for many analytes of clinical importance and inability to multiplex. Furthermore, the antibodies used in these devices suffer from product stability, slow and difficult manufacturing, and some require strict cold chain requirements that can be difficult to maintain. These points underscore the significance in developing robust and stable receptor molecules that can mimic biomolecules such as antibodies and enzymes.

As an alternative, MIPs can be used as artificial recognition molecules with the added advantage of rapid manufacturing at any scale. In addition to being used as artificial recognition molecules, MIPs have similar binding strengths as those seen in antibodies, can be stored dry for several years, reused hundreds of times before losing recognition capabilities, and can be rapidly manufactured at any scale. However, the use of MIPs as artificial antibodies is still not a possibility, as immunogenic antigens are typically larger than 6,000 Da. For many putative diagnostic devices, recognition of macromolecules such as 150 kD antibodies is necessary.

BRIEF SUMMARY

The following summary is provided to facilitate an understanding of some of the innovative features unique to the disclosed embodiments and is not intended to be a full description. A full appreciation of the various aspects of the embodiments disclosed herein can be gained by taking the entire specification, claims, drawings, and abstract as a whole.

It is, therefore, one aspect of the disclosed embodiments to provide for methods and systems for molecular imprinting.

It is another aspect of the disclosed embodiments to provide for the production of bio-inspired artificial antibodies with molecular imprinted silica particles.

The aforementioned aspects and other objectives and advantages can now be achieved as described herein. Methods and systems are disclosed for producing bio-inspired artificial antibodies with molecular imprinted silica particles. As the backbone monomer, tetraethyl orthosilicate can be used; and as active monomers, 3-Aminopropyl triethoxysilane, carboxybutyl 3-Amidepropyl triethoxysilane, and octyl triethoxysilane can be used. As a visualizing agent, carbon black can be added to the sol-gel process, yielding black silica particles. As a template, affinity purified mice West Nile antibody can be used.

The resulting molecularly imprinted polymers can be evaluated utilizing HPLC, centrifuge chromatography, spectrophotometry, and confocal microscopy to establish the importance of physiological pH matching during the synthesis process. Retention of antibody activity, imprinting factor, selectivity, and specific binding sites can be also determined. Physiological pH matching produced 160% more specific binding sites when compared to non pH matched molecular imprinting. For physiological pH imprinted particles, an eluted antibody has been found active and with a molecular imprinted polymers binding, for example, that is 3 times more antibody than controls with an 11 time higher fluorescence. In experimental embodiments, for example, it has been found that particles are also 23 times more selective for West Nile antibody than BSA or BGG.

Methods and systems for molecular imprinting are thus disclosed which include a molecular imprinting synthesis and matching a physiological pH of a template utilized in the molecular imprinting synthesis to achieve molecular imprinting. Molecular imprinting can be achieved by matching the physiological pH of the template used in a molecular imprinting synthesis. Furthermore, electrostatic charges can be complementary matched to the template by obtaining crystallographic data of a protein template. Particularly, positively and negatively charged aminoacids can be counted and matched by an oppositely charged monomer. For hydrophobic amino acids, isoleucin, leucin, and valine amino acids are counted. Since not all hydrophobic amino acids are exposed, the hydrophobic amino acid and hydrophobic monomer ratio can be determined experimentally by varying ratios from 1:1 to 1:10.

BRIEF DESCRIPTION OF THE DRAWINGS

The accompanying figures, in which like reference numerals refer to identical or functionally-similar elements throughout the separate views and which are incorporated in and form a part of the specification, further illustrate the present invention and, together with the detailed description of the invention, serve to explain the principles of the present invention.

DETAILED DESCRIPTION

Figure 1:
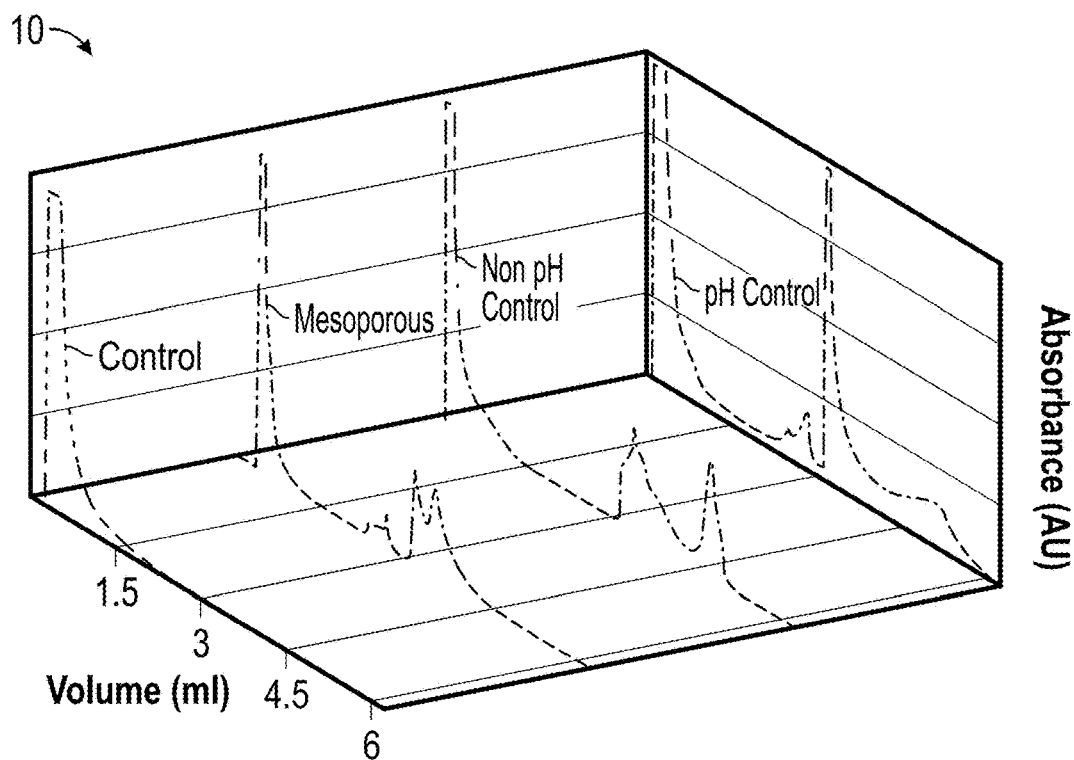
FIG. 1 illustrates a graph indicative of HPLC traces shown as a function of elution volume, in accordance with an example embodiment.

The particular values and configurations discussed in these non-limiting examples can be varied and are cited merely to illustrate at least one embodiment and are not intended to limit the scope thereof.

The embodiments will now be described more fully hereinafter with reference to the accompanying drawings, in which illustrative embodiments of the invention are shown. The embodiments disclosed herein can be embodied in many different forms and should not be construed as limited to the embodiments set forth herein; rather, these embodiments are provided so that this disclosure will be thorough and complete, and will fully convey the scope of the invention to those skilled in the art. For example, preferred and alternative embodiments are disclosed herein.

Additionally, like numbers refer to identical, like, or similar elements throughout, although such numbers may be referenced in the context of different embodiments. As used herein, the term "and/or" includes any and all combinations of one or more of the associated listed items.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Example embodiments involves the generation of MIPs from antibodies based on the use of charged monomers which counterbalance the surface charges of the antibody template. As monomers conform to the shape of the template, they are fixed by a rapid polymerization, permanently immobilizing them in a semi rigid network. It is hypothesized that the subsequent removal of the template leaves behind specific shape active sites allowing the polymer network to selectively recognize the original template. Example embodiments additionally involve the molecular imprinting of West Nile antibodies with a silica sol-gel process done under aqueous condition at a physiologically matched pH, in the presence of polymer grafted carbon black. Note that the term "West Nile" as utilized herein refers generally to the West Nile virus.

To determine if physiological pH matching in MIP synthesis had any effect, MIPs were encapsulated in a silica gel column to use with an HPLC system.

FIG. 1 illustrates a graph 10 indicative of HPLC traces shown as a function of elution volume, in accordance with an example embodiment. Traces are the following; column 1: control column with NIP; column 2: MIP synthesized with a mesoporous MIP formulation; column 3: MIP without pH control; column 4: MIP with physiological pH matching. At an elution volume of approximately 2.5 ml, the mobile phase was changed from 2×PBS to elution buffer on all columns.

FIG. 1 shows four HPLC traces obtained for NIPs, a mesoporous MIP formulation, a non pH matched MIP, and a physiological pH matched MIP, respectively where the whole West Nile antibody served as the template. Trace for the NIP showed only one peak corresponding to sample injection. This peak is present for all columns and is the column rejection of nonspecific molecules. No peaks were later detected for this column, indicating that no protein was retained in the column.

In an example embodiment, the columns packed with MIPs synthesized with and without pH control show peaks at an elution volume of 2.5 ml. Such an elution contained no protein measured by micro BCA and therefore the peak was attributed to be caused by the change of mobile phase. All MIP columns show peaks at an elution volume of 3 ml which is seen as a split peak for the mesoporous column and a single peak for the rest of the columns. The strongest peak observed came from column with the pH matched MIP. These peaks are attributed to the retention and elution of the antibody. The columns packed with MIPs that were synthesized with and without pH control also show an additional peak at elution volume of 4.2 ml, attributed to non-specifically bound antibody. Presence of WN antibody in collected aliquots was confirmed by western blot experiments.

Figure 2:
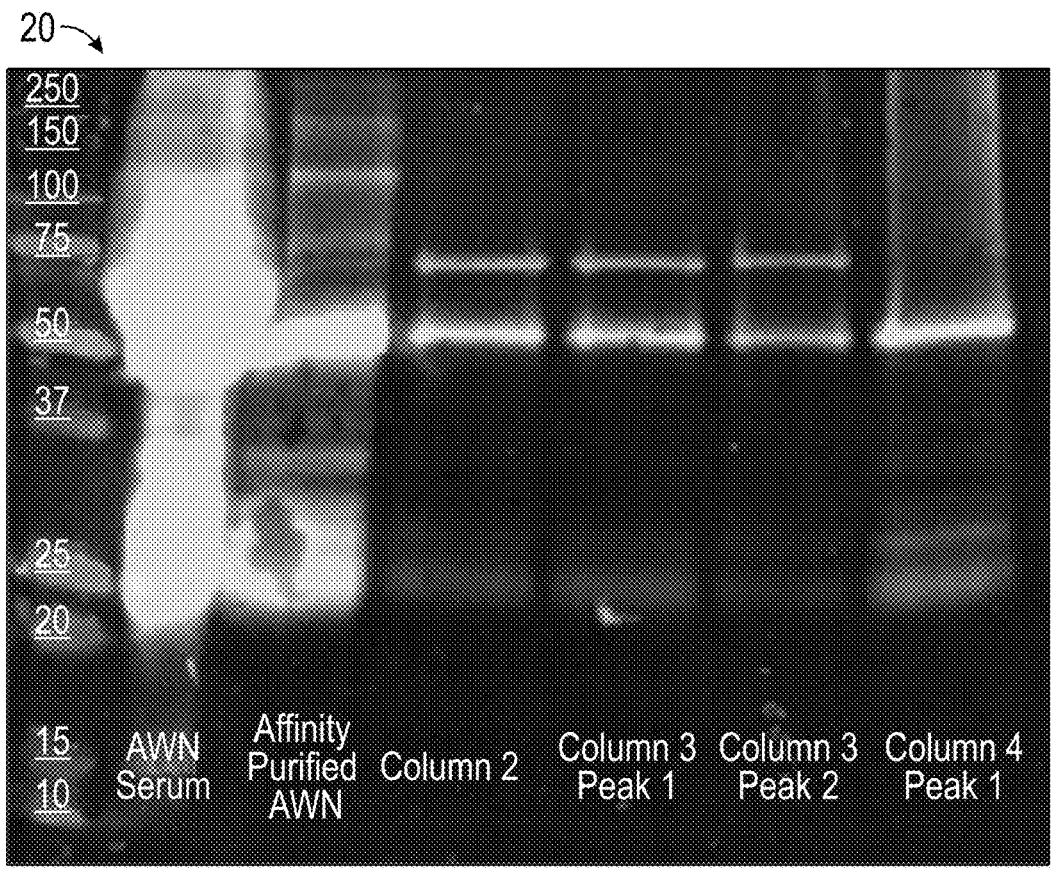
FIG. 2 illustrates an image of western blot of collected samples, in accordance with an example embodiment.
Figure 3A:
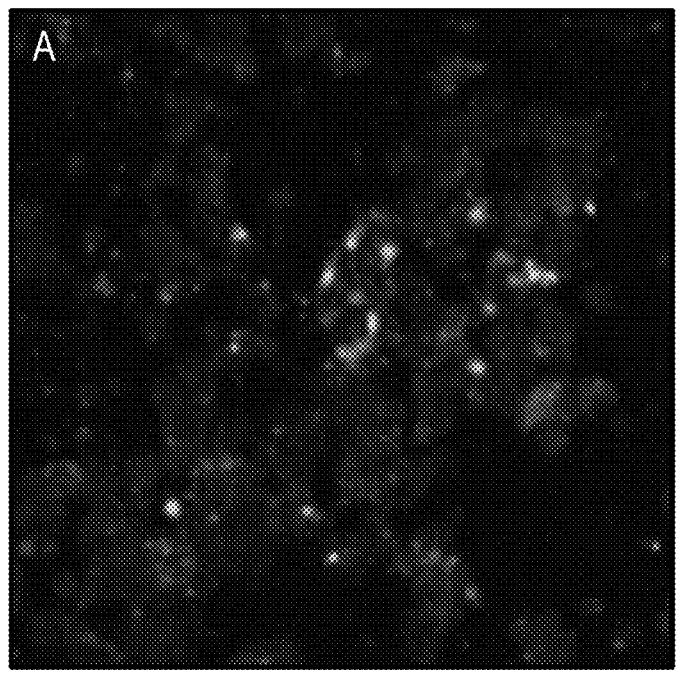
FIGS. 3A-3B illustrate examples of confocal images of MIP and NIP in the presence of fluorescently labeled AWN, in accordance with an example embodiment.
Figure 3B:
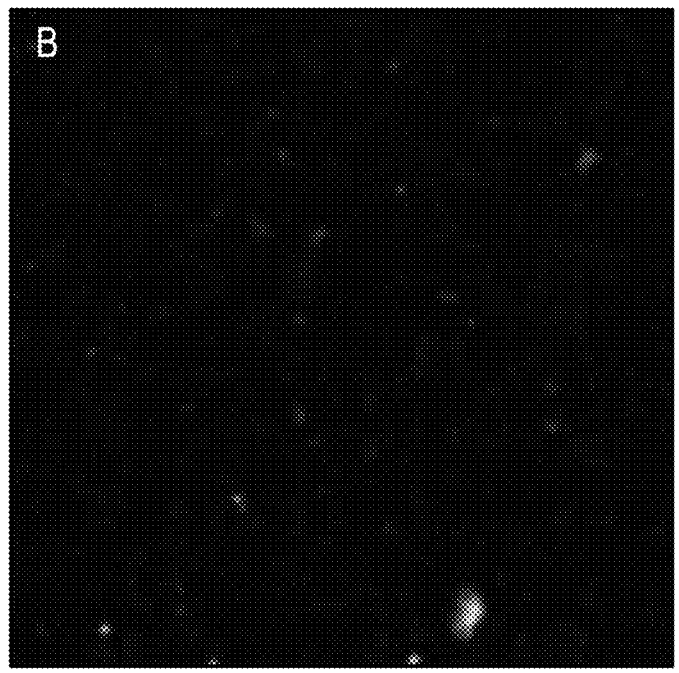
Figure 4:
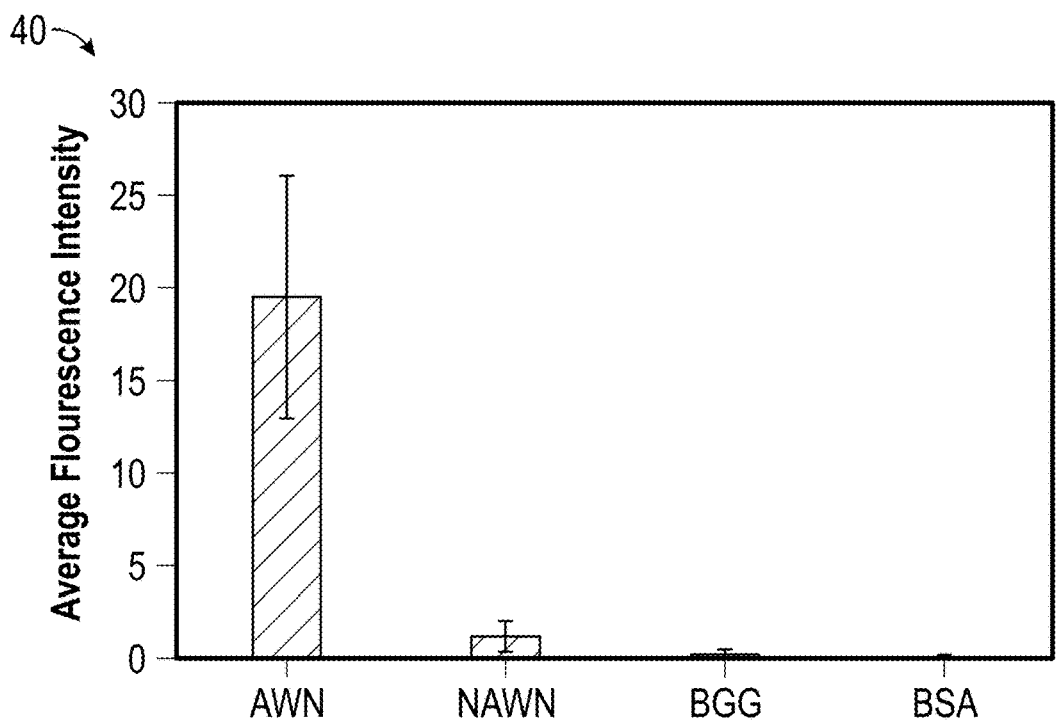
FIG. 4 illustrates a graph of data plotting the comparison of average fluorescence intensities of confocal images obtained, in accordance with an example embodiment.
Figure 5:
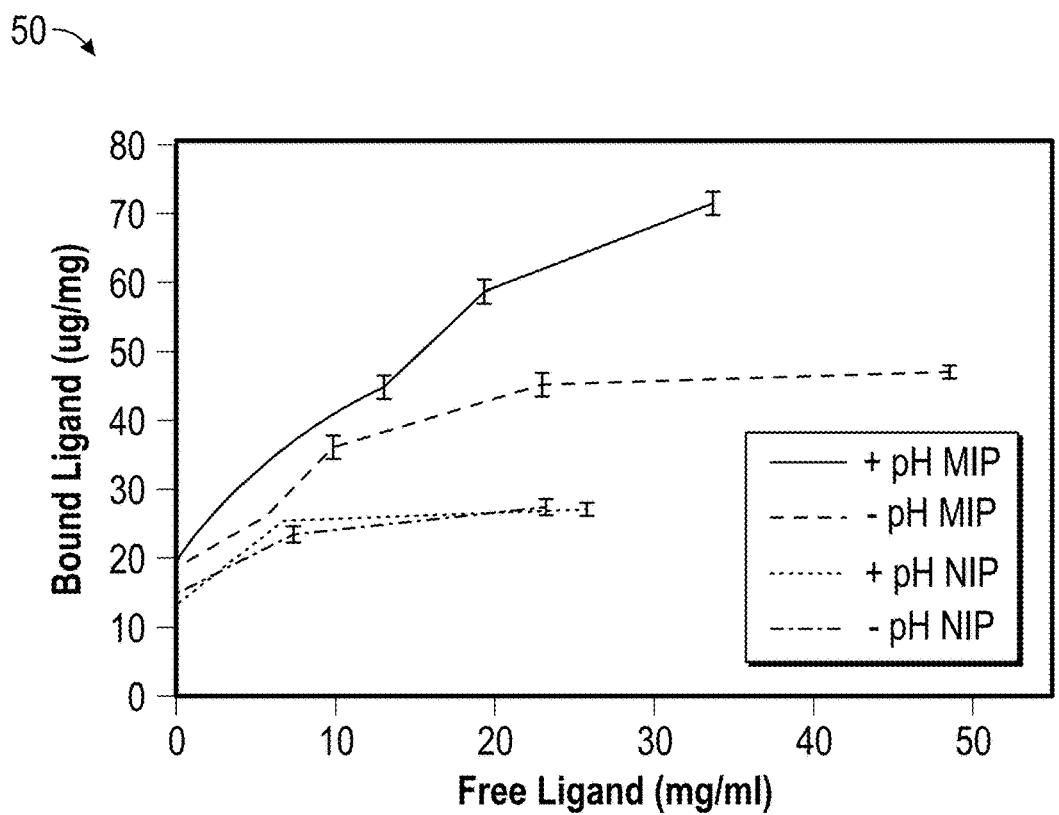
FIG. 5 illustrates a graph of data indicative of binding isotherms for both pH matched (+pH) and non pH matched (-pH) MIPs and NIPs rebinding the AWN template, in accordance with an example embodiment.

FIG. 2 illustrates an image 20 of a western blot of collected samples, in accordance with an example embodiment. In FIG. 2, from left to right, Column 1 represents a m.w. marker. Column 2 is AWN mice serum. Column 3 is affinity purified AWN. Column 4 is mesoporous MIP. Column 5 is MIP without pH control elution from HPLC peak 1. Column 6 is MIP without pH control elution from HPLC peak 2. Column 7 is physiological pH matched MIP from HPLC elution.

The image 20 of FIG. 2 thus demonstrates the western blot analysis of the elutions from the HPLC columns. Affinity purified antibody presents strong bands at 50 and 25 kDa in and corresponds to the heavy and light chain of the antibody; the presence of other bands are considered nonspecific or partially reduced proteins. Elutions from all MIP columns exhibited a common band at 50 kDa, the strongest band being observed for the pH matched MIP. The bands found at 25 kDa are also present in all elutions, with the elution from the pH matched MIP having the strongest signal. Thus, all imprints successfully captured WN antibodies. Bands at a molecular weight of ~70 kDa from elutions of the MIPs that were not pH balanced did not match any band of the purified antibodies. These bands are likely caused by the presence of nonspecific binding of other proteins present in the WN antibody serum used. HPLC and western blot data indicate that MIPs, prepared with careful pH control along the synthesis process, are able to retain full antibody template at much higher concentrations than MIPs that were synthesized with no pH adjustments or the mesoporous agent.

The activity of West Nile antibody, from the samples of the centrifuge columns, are shown in Table 1 below.

TABLE 1

ELISA readings of washed MIPs and NIPs

| 20X Wash | OD Reading | Interpretation | 5X Wash | OD Reading | Interpretation |
|---|---|---|---|---|---|
| MIP Elution 1 | 0.056 | Negative | MIP Elution 1 | 2.7 | Positive |
| MIP Elution 2 | 0.057 | Negative | MIP Elution 2 | 0.324 | Positive |
| NIP Elution 1 | 0.055 | Negative | NIP Elution 1 | 0.25 | Positive |

The data contained in Table 1 is based on experimental data in which MIPs were washed twice with either 20× or 5× elution buffer. NIPs were washed only once with 20× or 5× elution buffer.

A positive ELISA reading, as determined by negative and positive controls, was set to a cutoff value of 0.07 and a maximum value of 2.93. ELISA cutoff was determined by the average of 6 negatives samples plus 3 times standard deviation (XD+3SD). A positive reading for West Nile antibody was found for MIPs washed with 4 ml of PBS, the first and second elutions were collected. NIPs washed with 4 ml of PBS also retained active antibody for the first elution, no protein was detected on the second elution. MIPs washed with 16 ml of PBS retained no protein whatsoever, elution process did not recover any active antibody. Elisa studies indicates that peaks observed in HPLC traces are indeed active antibody retained by the pH controlled MIPs, although it is important to study the effect of particle washing to reduce nonspecific proteins while maintaining the captured antibody.

FIGS. 3A-3B illustrate example confocal images 32 and 34 of respective MIP and NIP in the presence of fluorescently labeled AWN, in accordance with an example embodiment. Clearly, the brightness of the MIPs indicates preferential binding after, for example, 6× volume washing. In image 32, pH matched MIPs are incubated with fluorescently labeled AWN. In image 34, NIPs are incubated with the fluorescently labeled AWN.

FIG. 4 illustrates a graph 40 of data plotting the comparison of average fluorescence intensities of confocal images obtained, in accordance with an example embodiment. In graph 40 of FIG. 4, each column represents the average of 4 or 8 images obtained per group. AWN column represents physiological pH matched MIPs in the presence of the labeled antibody. NAWN represents NIPs with the same antibody. BGG represents MIP and NIP particles with fluorescently labeled BGG. BSA represents MIP and NIP particles fluorescently labeled BSA.

Graph 40 thus demonstrates the average fluorescence intensity of the images. The fluorescence of MIPs bound to the template was 11 times higher than the fluorescence of NIPs. The selectivity for WN antibody template was 23 times higher than that of BSA or BGG in MIPs. There were no statistically significant differences between any of the controls. Confidence Student's t-test values were equal or less than 0.0015 for any control.

FIG. 5 illustrates a graph 50 of data indicative of binding isotherms for both pH matched (+pH) and non pH matched (−pH) MIPs and NIPs rebinding the AWN template, in accordance with an example embodiment. Binding isotherms are thus shown in FIG. 5. NIPs prepared with or without pH control absorbed about the same amount of West Nile antibody or 28 μg/mg. This is attributed to non-specific adsorption to the porous particles. MIPs prepared without pH control adsorbed about 48 μg antibody per mg MIP, a statistically different amount. MIPs prepared with pH control adsorbed approximately 80 μg antibody per mg MIP, also at a significant level. These data indicate that approximately 160% more specific binding sites are created using the pH controlled process.

Currently, the majority of imprinting technologies involve the synthesis and testing of MIPs in organic solvents. This is necessary as to increase short-range interactions between the template and MIP. In aqueous solutions, electrostatic and Van der Waals attractions are reduced due to competition between ions and water molecules, hence preventing a successful bind. Despite short interactions being saturated by ions and water molecules, natural antibodies are capable of displacing hydration layers blocking recognition sites with the aid of long range interactions. Once the hydration layer has been removed, an intimate contact with the antigen can be achieved. Since antibodies are successful in aqueous solutions, conditions for antibodies to bind antigen were investigated to generate bio-inspired molecular imprints.

The development of MIPs capable of template recognition in aqueous environments is of great importance as this greatly reduces materials and skills necessary for the recognition and separation of molecules of interest. Furthermore, solvent based MIPs are not likely to meet the ASSURED criteria for point of care devices due to the need of additional sample processing. To achieve macromolecular imprinting, the synthesis of molecular imprinted polymers (MIPs) must occur at an environment where the template can subsist for as long as the formation of the imprint.

Furthermore, since molecular imprinting must occur at the protein's native conformation state, labile proteins are likely to be denatured or an incorrect imprint could be formed. To develop improved molecular imprints, we focused initially on matching the synthesis pH to the template's physiological conditions as to retain conformation state as much as possible. The data presented here show that antibodies could be chosen as the template for MIPs and despite of them being known as labile molecules, they retain their conformational structure with little change for enough time for active monomers and TEOS to polymerize.

With the use of physiological pH matching, we achieved 160% more binding sites vs standard molecular imprinting. This increase in imprinting is due to greater preservation of the antibody template and better ionic complementarity, which is necessary for long-range interactions. Proteins, being zwitterions, can show different charges depending on pH, by fixating synthesis pH, molecular imprinting can counter match the physiological conformational structure of the template with the correct charges of the template. If pH is not controlled, molecular imprinting will counter act charges of the template not present at physiological conditions, all while imprinting the distorted conformational structure of the template.

The nature of MIPs being synthesized under specific conditions requires them to be tested under similar conditions as to present imprinted epitopes of the template. In the pH matching case, by using the same 0.03 M NaCl aqueous solution for binding experiments, the synthesis conditions are replicated closely enough to present imprinted epitopes of the template, whereas uncontrolled pH MIPs requires changing the testing solution to the synthesis pH and the template must go through a similar conformational deformation as the one caused during the molecular imprinting of the template; something difficult to replicate in a real life testing situation.

Although challenges in MIPs still exists, important advances have been achieved, such as MIPs produced by the epitope approach, where only a fraction of a molecule is used for MIP synthesis, in which later is able to recognize the whole molecule. Also, the use of MIPs as therapeutics in mice have been shown successful with the recognition and neutralization of mellitin in circulating blood and reduced mortalities vs control groups. With the addition of antibody imprinting, MIPs show potential as biological recognition molecules with the possibility of being used in diagnostic devices or as therapeutics.

Washing of the MIPs proved important. Depending on the assay developed, washing can be accomplished easily by removing supernatant by centrifugation and adding buffer to the test tube, or by flowing buffer through a lateral flow assay. After sample washing, the MIP selectivity can increase to, for example, 23. As an alternative, it may be possible to reduce non-specific binding by adding protein free blocking buffers. This might prove advantageous for portable and affordable assays, but the selectivity has not yet been determined. For example, by imprinting antibodies, MIPs could find applications in lateral flow assays to recognize the presence of specific antibodies in serum in order screen for infections.

Regardless of the method used, MIPs provide unique opportunities to low resource and medically underserved areas by providing with biorecognition molecules at a fraction of the price of antibodies. Furthermore, single use assays could be developed for individuals and MIP biosensors could be developed with the capability of being used for hundreds of times without losing their biorecognition capabilities, something not possible with antibodies.

In order to improve macromolecular imprinting, a bio-inspired synthesis has been developed. Molecular imprinting was achieved by matching the physiological pH. By reducing aggressive conditions during MIP synthesis, West Nile (WN) antibody imprinted silica particles were produced. These imprinted particles are stable for a large spectrum of temperature and pH ranges, thus potentially expanding diagnostics in low resource areas, remote settings, and agriculture. When prepared under physiological pH, imprinted particles could re-bind 52 μg of template per mg of particles, an improvement of 160% vs no pH controlled formulations, as determined by absorbance measurements, western blot, and HPLC. Fluorescently tagged West Nile antibodies showed 11 times higher fluorescence on pH matched MIPs when compared to NIPs with the same template. Also, MIP particles were 23 times more selective for West Nile antibody than BSA or BGG. The successful imprint of West Nile antibody, a 150 kDa molecule, will enable serum based diagnostics in low resource areas where traditional techniques may be less effective. As macromolecular imprinting becomes established, development of novel affordable and reusable assays, tailored to individuals or organizations, will become a possibility.

Tetraethyl orthosilicate (TEOS), 3-aminopropyl triethoxysilane (APS), and phosphate buffered saline as tablets were obtained from Sigma-Aldrich (St. Louis, Mo.) and used as is. Hydrochloric acid (37%), anhydrous acetic acid, and ethanol were acquired from Fisher Scientific (Pittsburgh, Pa.). Succinic anhydride, octyl trichlorosilane (OTS), ammonium hydroxide, ammonium bicarbonate, sodium hydroxide, and ATTO 495 nhs ester were obtained from Sigma-Aldrich. Polymer grafted carbon black was obtained by collecting ink from HP 33 cartridges (HP, Palo Alto, Calif.). According to literature, carbon black are 15 nm carbon particles grafted with 2-Pyrrolidone.

Ultrapure water was obtained from a Milli-Q Millipore unit with a water quality of at least 18.2 MΩ. Elution buffer was made with 0.15 M NaCl and 0.5% acetic acid. WN antibodies were obtained from hyper immune mouse ascitic fluid (HMAF). WN antibodies were purified by antibody affinity gel goat antibody to mouse IgG column from MP Biomedicals (Santa Ana, Calif.), following manufacturer's recommendations. Resulting antibodies were then desalted with Hitrap 5 ml desalting column (General Electric Healthcare Life Sciences, Wauwatosa, Wis.). Bovine serum albumin (BSA) and bovine gamma globulin (BGG) standard ampules were obtained from Thermo Scientific (Waltham, Mass.). For confocal imaging, WN antibody, BSA, and BGG were dyed using ATTO 495 nhs ester following manufacturer's recommendations at a protein concentration of 100 μg/ml.

Biomate 3 UV-Vis spectrophotometer was used for protein determination with BCA and micro BCA kits from Fisher Scientific. A GE Tricom 10/50 column was used for HPLC studies. Pierce centrifuge columns (Thermo Scientific, Waltham, Mass.) were used for ELISA tests. Carboxybutyl 3-Amidepropyl triethoxysilane (cAPS) was synthetized by reacting 5 ml of APS with 2.137 grams of succinic anhydride and adding ethanol to a final volume of 15 ml, the solution was left in a rotisserie overnight. The presence of carboxyl groups of cAPS was confirmed with a Thermo Nicolet Nexus FTIR. HPLC equipment consisted of a LabAlliance series 3 pump and UV-VIS model 500 detector with rise time set to 0.3 seconds and 0.001 AU sensitivity, and for data collection SRI model 333 integrator, a TSK gel size exclusion column G4000 and a Rheodyne injector model 9725i.

Imprinted silica particles can be prepared by, for example, a modified sol-gel method. Synthesis of imprinted particles was a four-step procedure, where the order in which the reagents were added proved essential. Briefly, for every 146 μl of TEOS, we used the following volumetric amounts of active monomers: 7.5 μl of APS, 36 μl of cAPS, and 43 μl of OTS. First, the active monomers were mixed in a centrifuge tube. Then, 365 μl of 0.03 M NaCl, 146 μl of TEOS, and 15 μl of black ink were added and mixed by pipetting in a new centrifuge tube. This was followed by adding 4-9 μl of ammonium hydroxide diluted 1:10 in deionized water as needed to adjust the solution's pH to 7.4. Lastly, 222 μl of WN antibody was added at a concentration of 200 μg/ml in 0.03 M NaCl buffer. The solution was pipette mixed and left overnight to complete the reaction. Non-imprinted particles (NIPs) were synthesized under identical conditions except for the last step where the WN antibody template was omitted. As control, MIPs were also prepared without the pH adjustment. As a second control, we used SDS as a porogen instead of the pH adjustment.

After synthesis, unreacted monomers were removed by centrifuging particles at 3200 RCF for 5 minutes and discarding supernatant. Then, template was eluted by adding 1.2 ml of elution buffer. Particles were resuspended in elution buffer by using an analog vortex mixer and if large particles were noted, particles were disrupted with up to 5 minutes of sonication with a Branson 2510 sonicator and remixed; the process was repeated once more. Afterwards, remaining template was eluted by suspending the particles in 1.2 ml of a 50% v/v mixture of glacial acetic acid and methanol and sonicated for 5 minutes. Particles were again centrifuged and the supernatant was discarded. The elution was continued until no trace of protein could be detected in the supernatant using a micro BCA kit. Particles were then washed in 0.03M NaCl buffer in triplicate, centrifuged, and resuspended in a final volume of 800 µl of 0.03M NaCl buffer and stored at room temperature until further use. After particle washing, a total of 7±2.45 mg of micro particles were collected.

Each MIP and NIP were transferred to an empty HPLC column, then immobilized in situ with silica gel. Gel was produced by adding 500 µl of TEOS to the column already loaded with MIPs, followed by the addition of 100 µl of APS, 25 µl of cAPS, 200 µl of ink, and 700 µl of ethanol. Afterwards, air was intentionally added by using a pipette and rough mixing of the solution for a minute. After approximately 45 minutes, solution gelled in the HPLC column with the MIPs. A total of 3 MIP and 3 NIP columns were produced.

Column packing was achieved by flowing 2×PBS at a maximum flow rate of 1 ml/min and maximum column backpressure of 150 psi repacking the column if needed. Column flow rates varied from 0.6 ml/min to 1 ml/min. The packed columns were equilibrated with elution buffer as the mobile phase until absorbance at 280 nm equilibrated. Afterwards column was re-equilibrated with 2×PBS. After equilibration, 60 µl of WN antibody serum sample was loaded to a 20 µl loop in the sample injector. Sample was then injected with a flow rate of 0.5 mil/min of 2×PBS as the mobile phase, the elution peak recorded and sample discarded.

After column re-equilibration, the mobile phase was changed to elution buffer at approximately 2.5 ml in order to elute retained antibody from the column. Peaks were recorded and eluted volumes were collected for western blot analysis. After collection, samples were desalted with 1×PBS buffer with a 5 ml desalting column. Samples were then compared against mouse ascitic fluid and affinity purified antibody controls with western blot to confirm the presence of West Nile antibody. Western blot was carried with a standard sds-page acrylamide gel. Volumes added per well were: 10 µl of molecular weight marker in well 1; 5 µl of WN antibody serum in well 2; 20 µl of affinity purified WN antibody in well 3; 45 µl of sample collected from column 2 in well 4; 45 µl of sample collected from column 3 peak 1 and 2 in well 5 and 6, respectively; and 40 µl of sample collected from column 4 in well 7. Volumes were estimated based on protein concentration of collected samples. All samples were treated with 2-mercaptoethanol to reduce disulfide bridges. After blotting, gel was transferred to nitrocellulose paper and developed with fluorescently labeled mice and rabbit anti-antibodies.

MIPs synthesized with pH control were encapsulated in gel as above and loaded to 5 ml centrifuge columns. A total of 2 MIP and 2 NIP columns were fabricated by loading each column with 800 µl of MIP or NIP gel and 4 ml of elution buffer. The columns were then centrifuged at 3200 RCF for 5 minutes. Partially compacted gels were re-suspended with 4 ml of elution solution with the aid of a vortex mixer. This process was repeated until 12 ml of elution buffer were used or no protein was detected in final elution with the micro BCA kit. Columns were then equilibrated with 4 ml of 2×PBS and centrifuged in duplicate.

For specificity testing, 60 µl of WN antibody serum was added to all columns along with 800 µl of 2×PBS, the gel was resuspended with a vortex mixer and the columns were incubated for 3 hours. After incubation, the columns were centrifuged for 5 minutes at 3200 RCF and the eluent was discarded. To reduce nonspecific binding, columns were washed with 5× or 20× the initial volume with PBS, 4 ml and 12 ml, respectively. To remove bound antibody, 800 µl of elution buffer was added. The gels were resuspended, centrifuged, the eluents were collected in a centrifuge tube, and protein presence was verified with UV-VIS. The elution was repeated and sample collected in a new centrifuge tube until no protein could be detected. The collected elutions were analyzed with an enzyme linked immunosorbent assay (ELISA) for WN antibody. Affinity purified antibody and PBS were used as positive and negative controls.

Vials of approximately 315 µg of MIPs in 240 µl of 0.03 M NaCl solution were loaded with nominal amounts of antibody as follows: 1.2, 2.4, 3.6, 4.8, 6.1, 12.6, 19, 25.2, 30, 48, 70, and 95 ug of antibody per mg of MIP. The exact antibody concentration was determined by micro-BCA. The exact concentrations of MIPs/NIPs were calculated by UV-Vis (610 nm) using a calibration curve that was obtained by measuring the absorbance of precisely weighted particles. The vials were left overnight in a rotisserie to reach equilibrium. Particles were then centrifuged at, for example, 3200 RCF for 5 minutes, the supernatant was collected and a micro BCA assay conducted. The centrifugation did not eliminate all particles from the suspension and therefore absorbance readings at 610 nm of control MIPs/NIPs without antibody were obtained and those baseline absorbances were subtracted from data. The free ligand concentration was calculated as the difference of the protein concentration in the supernatant after equilibrium and the baseline absorbance of virgin particles, normalized by volume. The bound ligand concentration was determined by the difference of the total antibody mass added to the particles less the free ligand mass, normalized by the mass of particles.

For confocal imaging, 30 µl of pH control MIPs were pipetted to a 0.6 ml centrifuge tube and 20 µl of ATTO 495 labeled WN antibody, with a protein concentration of 100 µg/ml, was added and the sample was gently mixed with the pipette. Afterwards, vials were left overnight in a rotisserie to reach equilibrium. Samples were then centrifuged, the supernatant discarded, and MIPs were washed twice with 300 µl of 0.03 M NaCl. Finally, particles were centrifuged and resuspended in 100 µl of 0.03M NaCl. As a control, MIPs were loaded with either ATTO 495 labeled BSA or BGG. As negative control, NIPs were also incubated with ATTO 495 labeled WN antibody, BSA or BGG. All tests were then repeated a total of 4 times.

Both a confocal and a standard brightfield image were obtained on an inverted Nikon Ti-U microscope, Nikon C1 confocal system, equipped with NIS elements and EZ-C1 software. The images were analyzed using Fiji image software. For brightfield images, all particles were counted using a particle analysis tool. For confocal images, a histogram was generated and all pixels above the signal noise were counted. To generate an average fluorescence intensity (AFI), confocal image's pixels were multiplied by their signal intensity, added together, and divided by total black pixels in the brightfield image.

Molecular imprinting can thus be achieved by matching the physiological pH of the template used in a molecular imprinting synthesis. Furthermore, electrostatic charges can be complementary matched to template by obtaining crystallographic data of the protein template. Particularly, positively and negatively charged aminoacids can be counted and matched by an oppositely charged monomer. For hydrophobic amino acids, isoleucin, leucin, and valine amino acids can be counted. Since not all hydrophobic amino acids are exposed, the hydrophobic amino acid and hydrophobic monomer ratio can be determined experimentally by varying ratios from 1:1 to 1:10.

Currently, there is a significant demand for affordable, robust, and stable receptor molecules that can mimic biomolecules such as antibodies and enzymes. As an alternative, molecular imprinting can be used as artificial recognition molecules to develop affordable diagnostics, with the added advantage of rapid manufacturing and indefinite shelf life at any temperature. Despite MIPs advantages, there are still limitations when imprinting molecules larger than 1,500 Da. To address such limitations, a bio inspired molecular imprinting formula as discussed herein has been developed.

To accomplish molecular imprinting of large molecules, in aqueous solutions, two important formulation parameters are addressed. The first parameter involves physiological pH matched synthesis, wherein molecular imprinting pH at synthesis is matched to the physiological pH of the template used. Physiological pH matching can be achieved by neutralizing the synthesis with hydrochloric acid or ammonium hydroxide as required, after a brief prehydrolization step. After the pH is matched, the template can be added and the synthesis left overnight.

The second parameter involves ionic monomer and template complementarity. By using the template's crystallographic data, positively and negatively charged amino acids are counted and counter matched to develop recognition sites that are complementary to the ionic amino acids in the desired template. In some example embodiments, a 1:1 ratio can be used in which every charged amino acid is countered with an opposite charged monomer at synthesis. For hydrophobic amino acids, isoleucin, leucin, and valine amino acids are counted. As indicated previously, since not all hydrophobic amino acids are exposed, the hydrophobic amino acid and hydrophobic monomer ratio is determined experimentally by varying ratios from 1:1 to 1:10.

Based on the foregoing, it can be appreciated that a number of example embodiments, preferred and alternative, are disclosed herein. For example, in one embodiment, a method of molecular imprinting can be implemented which involves the steps or operations of: configuring a molecular imprinting synthesis and matching a physiological pH of a template utilized in the molecular imprinting synthesis to achieve the molecular imprinting. In some example embodiments, the aforementioned matching can include a step or operation for complementary matching electrostatic charges to the template by obtaining crystallographic data of a protein template. In other example embodiments, the aforementioned matching further can include steps or operations for counting and matching positively and negatively charged amino acids by an oppositely charged monomer.

In some example embodiments, if the amino acids comprise hydrophobic amino acids, a step or operation can be implemented for counting isoleucin, leucin, and valine amino acids. In another example embodiment, a step or operation can be implemented for determining a hydroph amino acid and hydrophobic monomer ratio experimentally by varying ratios from a 1:1 ratio to a 1:10 ratio because not all of the hydrophobic amino acids are exposed. In other example embodiments, the molecular imprinting synthesis can be a physiological pH matched synthesis wherein a molecular imprinting pH at synthesis is matched to a physiological pH of the template.

In still another example embodiment, a physiological pH matching associated with the physiological pH matched synthesis can be achieved by neutralizing the synthesis with hydrochloric acid or ammonium hydroxide as required, after a prehydrolization step.

In yet another example embodiment, the complementary matching can involve ionic monomer and template complementarity wherein by using the crystallographic data of the data, positively and negatively charged amino acids are counted and counter matched to develop recognition sites that are complementary to ionic amino acids in a desired template.

In another example embodiment, the aforementioned template can comprise a West Nile antibody. In another example embodiment, the aforementioned West Nile antibody can be an affinity purified mice West Nile antibody.

In still another example embodiment, an apparatus for molecular imprinting can be implemented. Such an example apparatus can include a molecular imprinting synthesis and a template utilized in the molecular imprinting synthesis, wherein a physiological pH of the template utilized in the molecular imprinting synthesis is matched to achieve the molecular imprinting.

Methods and devices/apparatuses are thus disclosed for molecular imprinting include a molecular imprinting synthesis and matching a physiological pH of a template utilized in the molecular imprinting synthesis to achieve molecular imprinting. Molecular imprinting can be achieved by matching the physiological pH of the template used in a molecular imprinting synthesis. Furthermore, electrostatic charges can be complementary matched to the template by obtaining crystallographic data of a protein template. Particularly, positively and negatively charged amino acids can be counted and matched by an oppositely charged monomer. For hydrophobic amino acids, isoleucin, leucin, and valine amino acids are counted. Since not all hydrophobic amino acids are exposed, the hydrophobic amino acid and hydrophobic monomer ratio can be determined experimentally by varying ratios from 1:1 to 1:10.

It will be appreciated that variations of the above-disclosed and other features and functions, or alternatives thereof, may be desirably combined into many other different systems or applications. It will also be appreciated various presently unforeseen or unanticipated alternatives, modifications, variations or improvements therein may be subsequently made by those skilled in the art, which are also intended to be encompassed by the following claims.

What is claimed is:
1. A method of molecular imprinting, comprising:
configuring a molecular imprinting synthesis; and
matching a physiological pH of a protein template utilized in said molecular imprinting synthesis to achieve said molecular imprinting wherein said matching further comprises complementary matching electrostatic charges to said protein template by obtaining crystallographic data of the protein template, and counting and matching positively and negatively charged amino acids by an oppositely charged monomer.

2. The method of claim 1 further comprising, if said amino acids comprise hydrophobic amino acids, counting isoleucine, leucine, and valine amino acids.

3. The method of claim 2 determining a hydrophobic amino acid and hydrophobic monomer ratio experimentally by varying ratios from a 1:1 ratio to a 1:10 ratio because not all of said hydrophobic amino acids are exposed.

4. The method of claim 1 wherein said molecular imprinting synthesis comprises a physiological pH matched synthesis wherein a molecular imprinting pH at synthesis is matched to a physiological pH of said template.

5. The method of claim 4 wherein a physiological pH matching associated with said physiological pH matched synthesis is achieved by neutralizing said synthesis with hydrochloric acid or ammonium hydroxide as required after a prehydrolization step.

6. The method of claim 1, wherein said complementary matching involves ionic monomer and template complementarity wherein by using said crystallographic data of said data, positively and negatively charged amino acids are counted and counter matched to develop recognition sites that are complementary to ionic amino acids in a desired template.

7. The method of claim 1 wherein said template comprises a West Nile antibody.

8. The method of claim 7 wherein said West Nile antibody comprises an affinity purified mice West Nile antibody.

* * * * *